United States Patent [19]
Duncan

[11] Patent Number: 5,766,176
[45] Date of Patent: Jun. 16, 1998

[54] FORMABLE MESH

[75] Inventor: Jeffrey Duncan, Jacksonville, Fla.

[73] Assignee: Walter Lorenz Surgical, Inc., Jacksonville, Fla.

[21] Appl. No.: 712,292

[22] Filed: Sep. 11, 1996

[51] Int. Cl.[6] .................................................. A61B 17/80
[52] U.S. Cl. ................................................ 606/69; 606/73
[58] Field of Search .............................. 606/69, 70, 71, 606/72, 73, 60, 86

[56] References Cited

U.S. PATENT DOCUMENTS

| | | |
|---|---|---|
| 1,105,105 | 7/1914 | Sherman . |
| 2,494,229 | 1/1950 | Collison . |
| 2,791,868 | 5/1957 | Viken . |
| 3,547,114 | 12/1970 | Haboush . |
| 3,779,240 | 12/1973 | Kondo . |
| 4,219,015 | 8/1980 | Steinmann . |
| 4,503,848 | 3/1985 | Casper et al. . |
| 4,683,878 | 8/1987 | Carter . |
| 4,793,335 | 12/1988 | Frey et al. . |
| 4,903,691 | 2/1990 | Heinl . |
| 4,905,679 | 3/1990 | Morgan . |
| 4,905,680 | 3/1990 | Tunc . |
| 5,087,202 | 2/1992 | Krenkel . |
| 5,201,737 | 4/1993 | Leibinger et al. . |
| 5,346,492 | 9/1994 | Morgan ........................ 606/60 |
| 5,372,598 | 12/1994 | Luhr et al. . |
| 5,413,577 | 5/1995 | Pollock ......................... 606/69 |
| 5,468,242 | 11/1995 | Reisberg . |
| 5,578,036 | 11/1996 | Stone et al. ................... 606/69 |

FOREIGN PATENT DOCUMENTS

| | | |
|---|---|---|
| 290138 | 11/1988 | European Pat. Off. . |
| 291632 | 11/1988 | European Pat. Off. . |
| 433852 | 6/1991 | European Pat. Off. . |
| 2386-301 | 11/1978 | France . |
| 2631539 | 5/1988 | France . |
| 2806609 | 7/1979 | Germany . |

OTHER PUBLICATIONS

Hans G. Luhr, M.D., D.M.D., *Indications for Use of a Microsystem for Internal Fixation in Cranlofacial Surgery*, J. of Craniofacial Surgery, vol. 1, No. 1, Jan., 1990, pp. 35–52.

Translation of G 85 23 003.8 (Germany), Bone Plate, Feb. 1986, Oswald Leibinger Gmbh (Owner).

Codman & Shurtleff, *Neurosurgical Quality Instruments*, copyright 1965, pp. 10–13.

Howmedica International, Inc., *Vitallium—Verschiedene Implantate*, p. 54.

M.E. Müller, M. Allgöwer and H. Willenegger, *Manual of Internal Fixation*, copyright 1970, pp. 46 and 47.

U. Heim and K.M. Pfeiffer, *Internal Fixation of Small Fractures*, copyright 1974, 1982 and 1988, p. 60.

Walter Lorenz Surgical, Inc., *Surgical Instrument Catalog 5th Edition*, copyright ©1993, pp. 10–11.

Walter Lorenz, Surgical, Inc., 1.5/2.0mm Combination Titanium Osteosynthesis System, copyright 1994.

Leibinger LP, *Leibinger*, copyright 1995, (1 sheet).

For The Few Who Know The Difference, TiMesh Inc. (1 sheet).

*Primary Examiner*—Guy V. Tucker
*Attorney, Agent, or Firm*—Harness, Dickey & Pierce, P.L.C.

[57] ABSTRACT

This invention relates to a formable mesh for use in osteosynthesis and a method of use therefore. The formable mesh includes a plurality of orifice plates linked together by a plurality of connecting arms. The plurality of orifice plates includes a first orifice plate having at least six radially offset connecting arms. Each of the radially offset connecting arms includes a first end coupled to the first orifice plate and a second end coupled to a second orifice. Upon rotation of the first orifice plate in a first direction, each of the second orifice plates is retracted relative to the first orifice plate. Upon rotation of the first orifice plate in a second direction, each of the second orifice plates is extended relative to the first orifice plate.

31 Claims, 7 Drawing Sheets

PRIOR ART

FIG. 1A.

PRIOR ART

FIG. 1B.

PRIOR ART

FIG. 2.

PRIOR ART

FORMABLE MESH

BACKGROUND OF THE INVENTION

1. Field of the Invention

This invention relates generally to a formable mesh for use in osteosynthesis and, more particularly, to a formable mesh that may be shaped three-dimensionally to conform to a desired anatomical shape.

2. Discussion of the Related Art

During cranial and facial surgery it is sometimes necessary to surgically align, stabilize, fasten or join bone using mechanical means, known in the art as osteosynthesis. Use of cranial and facial osteosynthesis may arise during reconstructive, plastic or neurosurgery. For example, during reconstructive surgery, various fragments of a fractured skull may be required to be surgically fastened or joined together using mechanical means. During neurosurgery, bone flaps which are removed to gain access to the brain generally require mechanical means to secure the bone flaps in place after the bone flaps are separated from the skull. During plastic surgery, various cranial and facial features may be modified by relocation of the bone to provide a desired effect which also requires mechanical means to join or fasten the surgically separated bone.

Figure 2:
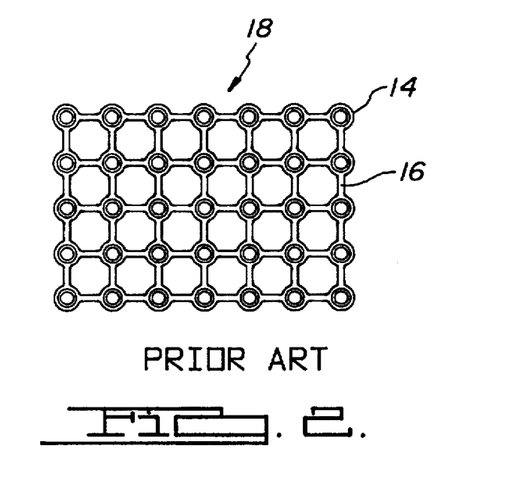
FIG. 2 is a top planar view of a prior art uniform grid panel.
Figure 3:
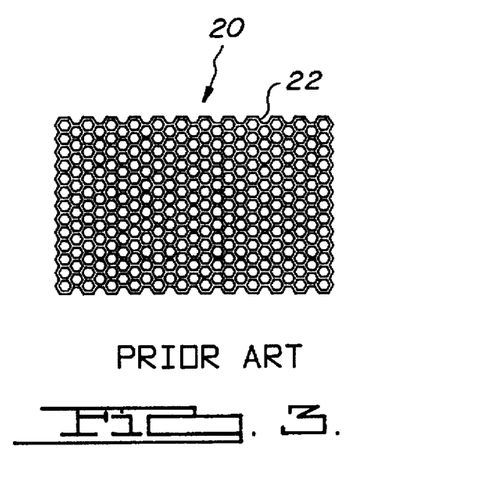
FIG. 3 is a top planar view of a prior art flexible mesh.

The conventional mechanical means used to fasten, join and secure in place cranial and facial bone for fixation and immobilization include preconfigured plates (see FIGS. 1A and 1B), uniform grid panel (see FIG. 2) and flexible mesh (see FIG. 3). Each of these devices are generally secured or affixed to the skull by use of screws or other appropriate fastening mechanisms to join, secure and immobilize portions of the bone in a substantially fixed relationship with respect to one another. The preconfigured plates are generally utilized on smooth, slightly curved portions of the skull, while the uniform grid panel and the flexible mesh are generally utilized along areas of the skull having complex three-dimensional contours or surfaces.

Figure 1A:
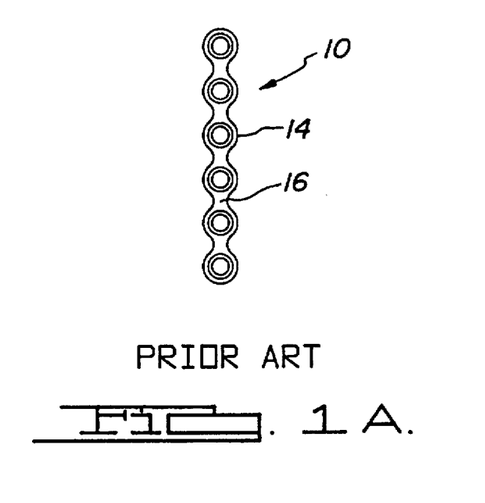
FIG. 1A is a top planar view of a prior art preconfigured straight-shaped plate.
Figure 1B:
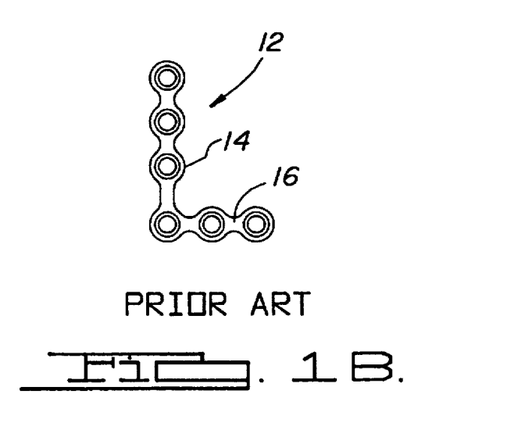
FIG. 1B is a top planar view of a prior art preconfigured L-shaped plate.

The preconfigured plates include straight-shaped plates 10, as shown in FIG. 1A, and L-shaped plates 12, as shown in FIG. 1B. The preconfigured plates also include various other shaped plates such as T-shaped plates, Z-shaped plates, Y-shaped plates, square-shaped plates, triangular shaped plates, etc. Each of these preconfigured plates includes annular tabs 14 linked together by linking members 16. The preconfigured plates are generally flat and are subsequently shaped by hand to form a slight curve which conforms to the curvature of the skull. Other prior art preconfigured plates are also provided with a pre-shaped curve to generally conform to the slight curvature of the skull. The uniform grid panel 18, as shown in FIG. 2, also includes the annular tabs 14 connected together by the linking members 16. In this manner, when a surgeon requires a particular shape, the surgeon cuts along the linking members 16 to form a desired configuration or shape. Likewise, the flexible mesh 20 as shown in FIG. 3, is merely an interconnected series of members 22 forming the flexible mesh 20 similar to a screen. Here again, the surgeon cuts the mesh 20 into a desired configuration similar to the way a patch would be cut to cover a desired area.

Figure 4:
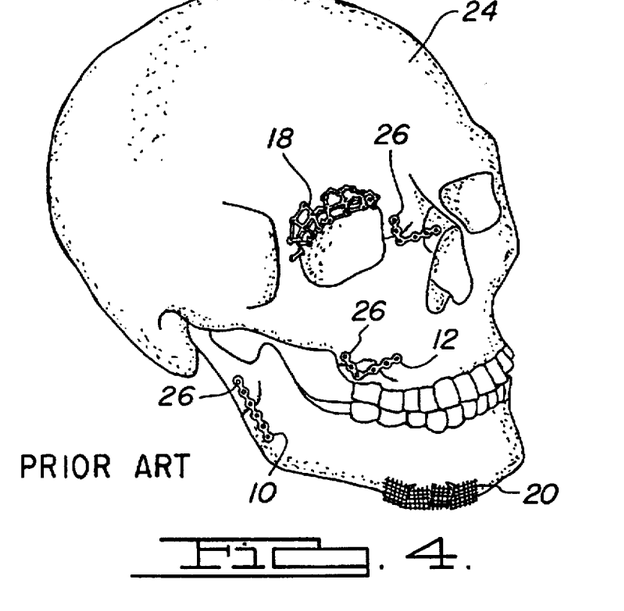
FIG. 4 is a perspective view of a skull which employs the prior art devices.

As shown in FIG. 4, the preconfigured straight-shaped plate 10 and the L-shaped plate 12 are shown affixed to a skull 24 with mounting screws 26. The straight-shaped plate 10 and the L-shaped plate 12 are shown affixed to various curved portions of the skull 24 to fixedly hold and secure one portion of the bone relative to another portion of the bone. Patches formed by the uniform grid panel 18 and the flexible mesh 20 are also shown affixed at various portions of the skull 24 with the mounting screws 26. As observed from FIG. 4, the preconfigured plates 10 and 12 are generally used only where there are slight curvatures, while the grid panel 18 and the flexible mesh 20 are utilized along various complex three-dimensional surfaces of the skull 24.

Use of the above-identified bone fixation devices fixedly secures and immobilizes portions of the bone. However, use of the above-identified bone fixation devices exhibit many disadvantages. For example, the preconfigured plates are generally not flexible enough to be shaped to conform to complex three-dimensional surfaces of the skull, such as an eye socket or around the jaw bone. Use of the grid panel 18 or the flexible mesh 20 along such complex three-dimensional surfaces is an improvement. However, the uniform grid panel 18 and the flexible mesh 20 generally cannot be compressed or stretched to the necessary degree to form a relatively smooth surface. Because of this, kinking, overlapping edges and raised areas generally result (see FIG. 4) upon shaping the uniform grid panel 18 and the flexible mesh 20 to meet the complex three-dimensional surfaces of the skull. Moreover, in many instances, portions of the grid panel 18 or the flexible mesh 20 must be cut out in order to enable these devices to be bent and formed around substantially sharp contours (see FIG. 4).

U.S. Pat. No. 5,468,242 to Reisberg addresses some of the above-identified concerns by providing a mesh implant having pre-bent arms which are capable of being compressed or stretched during shaping of the mesh along the three-dimensional contours of the skull. However, use of this mesh also has inherent disadvantages. For example, because Reisberg is based on buckling of the bendable arms, upon stretching or compressing the bendable arms to conform to the contour of the skull, kinks may nevertheless result between the positioning of the mounting screws. These kinks require a surgeon to either attempt to physically compress the secured mesh against the skull by hand, after it has been secured with the mounting screws, or require the removal and repositioning of the mounting screws. The bendable arms also reduces the overall strength of the mesh as compared to a mesh having straight arms which are always under tension. Reisberg also generally moves along only two principle directions or axes as it is compressed or stretched since it is based generally on a square-type grid pattern. Such movement along only two principle planar directions further limits the formability of this mesh especially along spherical contours. Reisberg further provides only a uniform repeated mesh pattern which also limits its formability along extreme surface contours.

What is needed then is a formable mesh for use in osteosynthesis which does not suffer from the above mentioned disadvantages. This will, in turn, provide a formable mesh which can be smoothly shaped along complex three-dimensional contours, reduce the amount of time required to shape the formable mesh, reduce the overall surgical cost, enable movement in at least three principle directions for increased formability, enable self-tightening or compression capabilities upon securing the formable mesh, provide for extension and contraction based on both rotation and on compression and expansion of the formable mesh, provide for alternating patterns that enables formability to very small spherical surfaces without kinks or overlaps, provide for connecting arms forming a series of these contiguous parallelograms each having a common corner and each sharing a common side which may be compressed or expanded along three principle directions and provide for radially offset connecting arms which form parallelograms such that adjacent orifice plates can be extended or retracted by increasing or decreasing the angle or length of the radially offset connecting arms. It is, therefore, an object of the present invention to provide such a formable mesh and a method of use therefore.

SUMMARY OF THE INVENTION

In accordance with the teachings of the present invention, a formable mesh for use in osteosynthesis is disclosed. The formable mesh is adapted to be shaped to conform to complex three-dimension contours or surfaces. This is basically achieved by providing a formable mesh which may be shaped by both rotation and by compression and expansion of the formable mesh.

In one preferred embodiment, a formable mesh for use in osteosynthesis includes a plurality of orifice plates linked together by a plurality of connecting arms. The plurality of orifice plates includes a first orifice plate which has at least six radially offset connecting arms. Each of these radially offset connecting arms includes a first end which is coupled to the first orifice plate and a second end coupled to a second orifice plate. Upon rotation of the first orifice plate in a first direction, each of the second orifice plates is retracted relative to the first orifice plate. Upon rotation of the first orifice plate in a second direction, each of the second orifice plates is extended relative to the first orifice plate.

In another preferred embodiment, a formable mesh for use in osteosynthesis includes a plurality of orifice plates and a plurality of connecting arms linking together the plurality of orifice plates. The plurality of connecting arms forms a plurality of quadrilaterals. This plurality of quadrilaterals forms a series of three contiguous quadrilaterals each having a common corner and each sharing a common side. This series of three contiguous quadrilaterals are operable to be compressed and expanded along three principle directions to conform the formable mesh to a three dimensional contour.

Use of the present invention provides a formable mesh for use in osteosynthesis. As a result, the aforementioned disadvantages associated with the currently available techniques for use in osteosynthesis have been substantially reduced or eliminated.

BRIEF DESCRIPTION OF THE DRAWINGS

Still other advantages of the present invention will become apparent to those skilled in the art after reading the following specification and by reference to the drawings in which.

DETAILED DESCRIPTION OF THE PREFERRED EMBODIMENT(S)

The following description of the preferred embodiments concerning a formable mesh for osteosynthesis is merely exemplary in nature and is in no way intended to limit the invention or its application or uses. Moreover, while the present invention is described in detail below with reference to cranial and facial osteosynthesis, it will be appreciated by those skilled in the art that the present invention is clearly not limited to cranial and facial osteosynthesis and may be utilized in various other surgical procedures.

Figure 5:
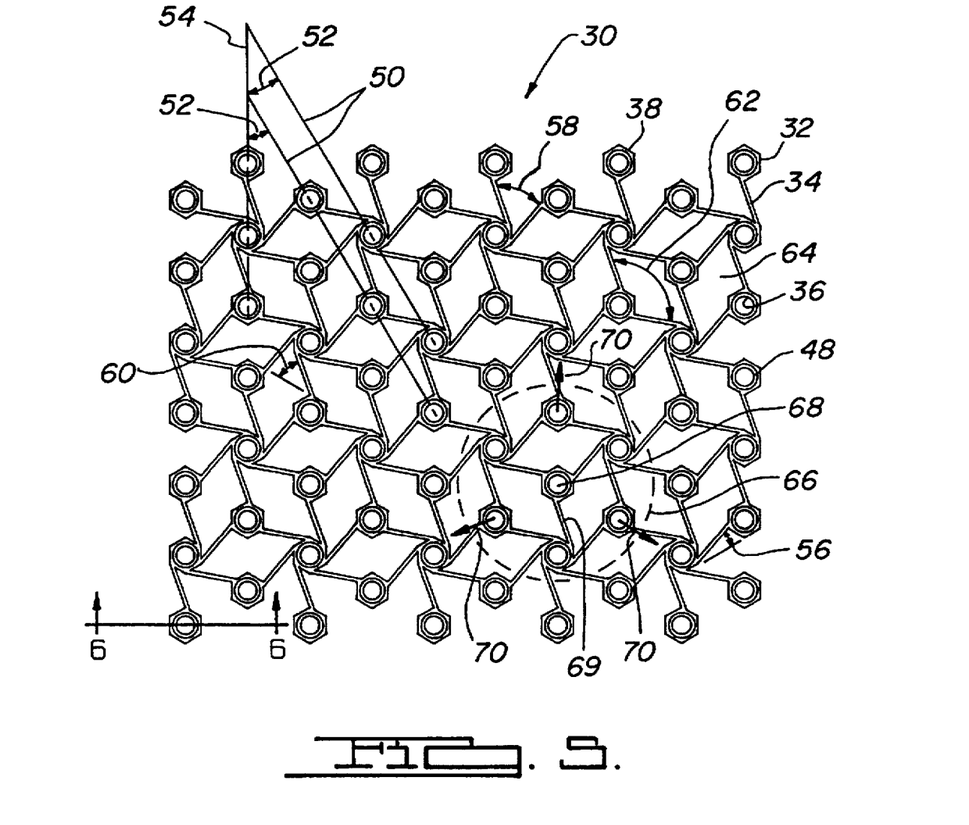
FIG. 5 is a top planar view of the formable mesh according to the teachings of a first preferred embodiment of the present invention.

Referring to FIG. 5, a formable mesh 30 according to the teachings of a first preferred embodiment of the present invention is shown. The formable mesh 30 is preferrably constructed of titanium. However, the formable mesh 30 may also be constructed of a titanium alloy, cobalt-chrome, stainless steel, resorbable polymer or any other biocompatible implant material having a malleable property so that the formable mesh 30 may be smoothly shaped to conform to complex three-dimensional contours or surfaces of the skull 24.

Figure 6:
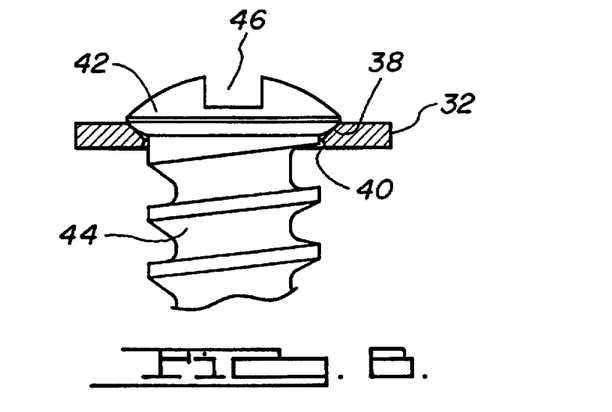
FIG. 6 is a partial side cross-sectional view of the formable mesh taken along line 6—6 of FIG. 5 illustrating one method of mounting the formable mesh.

The formable mesh 30 includes a plurality of orifice plates 32 linked or connected together by a plurality of integrally coupled connecting arms 34. Each orifice plate 32 preferably includes and defines a circular orifice 36 having a diameter in the range of about 0.7 millimeters to about 2.5 millimeters, with 1.5 millimeters being the preferred diameter. Concentric with each circular orifice 36 is a counterbore 38 and a reverse taper 40. The counterbore 38 is operable to nestingly receive a head 42 of a mounting screw 44 or other suitable mounting device (see FIG. 6). The mounting screw 44 is also preferrably constructed of titanium or other suitable biocompatible material. The mounting screw 44 includes a cross-drive head 46 or other suitable head such as a square-drive head or an internal hexagon-drive head.

The outer periphery 48 of the orifice plates 32 are each formed as a hexagon. Those skilled in the art would also recognize that the outer periphery 48 may also include any other shape such as a circle, square, octagon, etc. The side to side width of the hexagon orifice plate 32 is about 2.25 millimeters and the point to point or corner to corner width is about 2.7 millimeters. The formable mesh 30 has a substantially uniform thickness along both the orifice plates 32 and the integrally coupled connecting arms 34 in the range of between about 0.1 millimeters to about 1.0 millimeter. Preferably, the thickness will either be 0.3 millimeters or 0.6 millimeters. This enables the formable mesh 30 to be sufficiently malleable to be smoothly shaped or formed to the complex three-dimensional surface or contour of the skull 24. The thickness of the formable mesh 30 will vary depending on where the formable mesh 30 is utilized on the skull 24 and whether or not it is in a load bearing or a nonload bearing situation. The integrally coupled connecting arms 34 have a width of about 0.4 millimeters. Those skilled in the art would also recognize that the dimensions of the formable mesh 30 provided herein are merely exemplary in nature and the formable mesh 30 may therefore be constructed having various other dimensions.

The formable mesh 30 includes an alternating series of orifice plates 32 either having six (6) tangential connecting arms 34 or three (3) connecting arms 34. Upon a close review of the formable mesh 30 in FIG. 5, one can readily observe that the orifice plates 32 having six (6) connecting arms 34 occur along parallel planes 50 at an angle 52 of about 30° relative to a vertical plane 54. Likewise, the orifice plates 32 having the three (3) connecting arms 34 also occur along parallel planes 50 at the angle 52 of about 30° relative to the vertical plane 54.

Each connecting arm 34 is pre-rotated counterclockwise and radially offset along an orifice plate 32. Each six-arm orifice plate 32 has six (6) connecting arms that are tangential to the orifice plate 32 and angle off counter-clockwise along each side of the outer periphery 48 of the hexagon. The angle 56 of each connecting arm 34 is about 20.7° relative to a side of the hexagon. The angle 58 between each connecting arm 34 is about 60°. Each three-arm orifice plate 32 has three (3) connecting arms 34 angling off counter-clockwise along every other corner of the outer periphery 48 of the hexagon at an angle 60 of about 42° relative to a side of the hexagon. The angle 62 between each connecting arm 34 is about 120°. Those skilled in the art would also recognize that each connecting arm 34 could be connected perpendicular to the orifice plates 32 or at another angle.

The interconnected alternating series of three-arm orifice plates 32 and six-arm orifice plates 32 forms or defines a plurality of angled quadrilaterals 64, shown here as parallelograms 64. Those skilled in the art would also recognize that various other shaped and angled quadrilaterals could also be used. The plurality of parallelograms 64 are substantially formed by the radially offset connecting arms 34. The alternating pattern or series of three-arm orifice plates 32 and six-arm orifice plates 32 form a series or plurality of three (3) adjacent or contiguous angled parallelograms 66 having a common corner 68 with each sharing a common side 69, which enables movement along three principle planar directions identified by arrows 70. The series of three (3) parallelograms 66 is based on three (3) of the six (6) axes that divide a hex (i.e. three (3) of the six (6) connecting arms 34 of a six-arm orifice plate 32). This alternating pattern or series that forms the parallelograms 64 enable the formable mesh 30 to be shaped or contoured by compressing or expanding the parallelograms 64 along or in at least the three principle directions 70 at the same time. This ultimately enables the formable mesh 30 to be shaped or contoured along a concave or convex spherical radius as small as about 15 millimeters without any kinks or overlaps occurring in the formable mesh 30.

Figure 7:
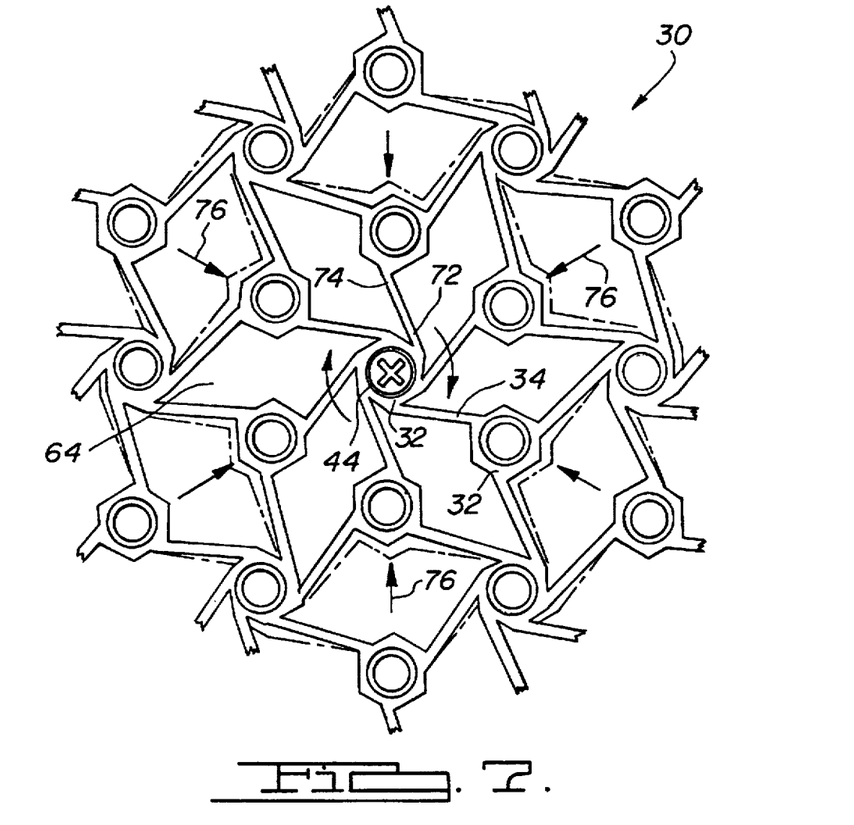
FIG. 7 is a top planar view of the formable mesh of FIG. 5 shown with a portion being compressed upon being rotated.

Referring to FIG. 7 another feature of the formable mesh 30 will now be described in detail. FIG. 7 shows a portion of the formable mesh 30 which includes a first six-arm orifice plate 32 having six (6) counter-clockwise angled off connecting arms 34. Each connecting arm 34 includes a first end 72 integrally coupled to the six-arm orifice plate 32 and a second end 74 integrally coupled to a second three-arm orifice plate 32. This forms a series of six (6) adjacent or contiguous parallelograms 64 having a substantially common corner centered about the six-arm orifice plate 32 that forms essentially a shape of star. Positioned within the six-arm orifice plate 32 is a mounting screw 44.

Upon tightening the mounting screw 44 or turning it clockwise, the head 42 of the mounting screw 44 is nestingly received within the counterbore 38. Upon the head 42 engaging the counterbore 38, the frictional force causes the six-arm orifice plate 32 to rotate in a first clockwise manner or direction. This subsequently causes the six (6) three-arm orifice plates 32 to be drawn into the six-arm orifice plate 32 or retracted relative to the six-arm orifice plate 32 (see phantom lines), as the six (6) connecting arms 34 are generally slightly wrapped or drawn around the six-arm orifice plate 32. This retraction or compression shown by the arrows 76 creates an automatic self-tightening and self-aligning effect on the formable mesh 30, as the formable mesh 30 is being secured to a portion of the skull 24. In other words, as the mounting screw 44 is tightened down, the formable mesh 30 is automatically tightened or cinched smoothly against the contour or surface of the skull 24 by drawing the other orifice plates 32 together. Therefore, any slight ripples will be automatically removed upon securing the formable mesh 30 to the surface of the skull 24. This surface may be a flat planar surface, a concave surface, a convex surface, or any other complex three-dimensional surface.

As the six (6) connecting arms 34 are drawn or wrapped around the six-arm orifice plate 32, the six (6) connecting arms 34 slightly curve or arc adjacent to the first end 72, while the remaining portion or majority of the connecting arm 34 remains generally straight. The connecting arms 34 remain generally straight with a slight arc, assuming the formable mesh 30 is positioned on a planar surface, because the connecting arms 34 are under tension. Should the formable mesh 30 be positioned on a concave or convex spherical surface, upon looking down atop the formable mesh 30 the connecting arms 34 are generally straight linearly, while they may have an arcuate or curved portion conforming to the contour of the skull 24.

Conversely, should the six-arm orifice plate 32 be rotated in a second counter-clockwise direction, each of the second three-arm orifice plates 32 coupled to the six (6) connecting arms 34 are extended away from or relative to the six-arm orifice plate 32, generally opposite in the direction of arrows 76. This rotation can occur by pulling opposite along each of the axes identified by the arrows 76. This causes each of the six (6) connecting arms 34 to be slightly curved or arced adjacent to the first end 72 in a clockwise manner, while the remaining portion of the connecting arms 34 contain a slight arc or remain generally straight. Accordingly, one skilled in the art would readily recognize upon review of FIGS. 5 and 7 that the formable mesh 30 may be shaped and contoured in two ways. Specifically, by compressing or expanding the parallelograms (see FIG. 5) or by rotation of the orifice plates 32 (see FIG. 7). Upon rotation, the angle of each of the angled off or pre-rotated connecting arms 34 is either increased or decreased, while the adjacent orifice plates 32 are extended or retracted, respectively.

As observed from FIG. 7, since the six (6) radially offset connecting arms 34 of the six-arm orifice plate 32 are angled off in a counter-clockwise direction and rotation in a clockwise direction compresses or tightens the formable mesh 30, the formable mesh 30 requires the correct side to be facing opposite the surface which it is placed against. In order to identify this correct side, the correct side of the formable mesh 30 may be chemically etched with the words "Up" uniformly stencilled across the formable mesh 30 or other suitable method. It should also be noted that the three (3)

radially offset connecting arms 34 of the three-arm orifice plates 32 are also angled off counter-clockwise so that the entire formable mesh 30 uniformly rotates in one of two directions, thereby eliminating any binding upon rotation of any adjacent orifice plates 32. In other words, upon rotation of any orifice plate 32 in a clockwise manner during securing of the formable mesh 30, the formable mesh 30 will be uniformly cinched and tightened down smoothly against the surface contour. This is in contrast to a situation where turning one orifice plate clockwise tightens the mesh and turning another adjacent orifice plate clockwise loosens or expands the mesh.

Figure 8A:
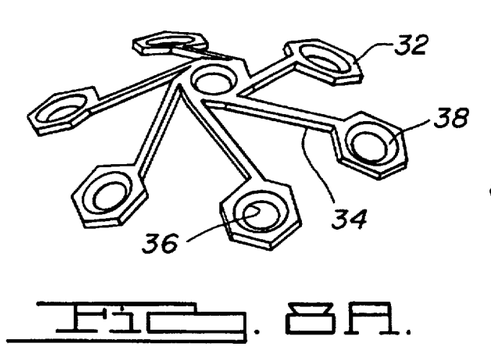
FIGS. 8A and 8B are perspective views of a portion of the formable mesh of FIG. 5 shown shaped with three-dimensional contours.
Figure 8B:
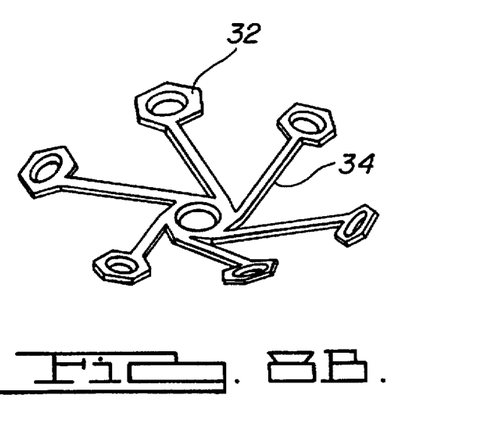

Referring to FIGS. 8A and 8B, portions of the formable mesh 30 are shown shaped with a three-dimensional contour. Specifically, in FIG. 8A, the six-bar orifice plate 32 is shown on a plane above the three-arm orifice plates 32 and in FIG. 8B, the six-arm orifice plate 32 is shown on a plane below the six (6) three-arm orifice plates 32. Upon moving the six-arm orifice plate 32 either above or below the six (6) three-arm orifice plates 32, the six-arm orifice plate 32 rotates counter-clockwise as it moves upward along the z-axis or clockwise as it moves downward along the z-axis.

Figure 9:
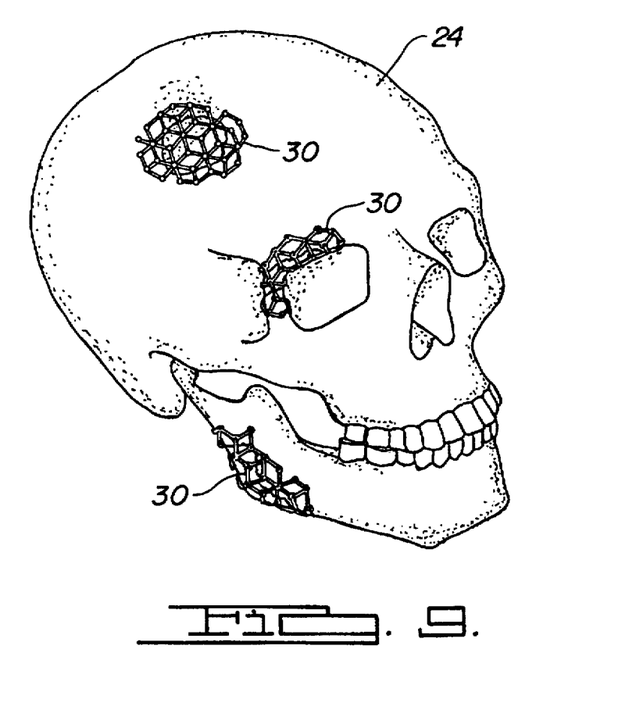
FIG. 9 is a perspective view of a skull which employs the formable mesh according to the teachings of the preferred embodiment of the present invention.

Referring to FIG. 9, the skull 24 is shown having the formable mesh 30 secured to portions of the skull 24 with mounting screws 26. Upon review of FIG. 9, one can readily observe that the formable mesh 30 can be positioned smoothly along various complex three-dimensional surface contours of the skull 24.

The method of using the formable mesh 30 will now be described as used in an osteosynthesis surgical procedure. It is to be understood, however, that the formable mesh 30 may be used with other surgical procedures as well. First, a surgeon will determine the size of the patch required to cover the desired surface area of the bone. Once a size is determined, a surgeon will either select the proper sized formable mesh 30 which will be provided generally having a square periphery (see FIG. 5) or the surgeon will merely cut the particular size required along the connecting arms 34. The surgeon will then generally first form the formable mesh 30 by compressing and expanding the formable mesh 30 along the three planar principle axes by compressing and expanding the parallelograms 64.

Once the formable mesh 30 is generally shaped to the surface contour desired, the surgeon will then start inserting mounting screws 44 along desired areas. Upon tightening the mounting screws 44, the formable mesh 30 is automatically self-aligned, tightened and compressed along these areas to further automatically smooth out any wrinkles, thereby providing a substantially smooth surface which follows the contour of the surface area being covered. These two ways of shaping the formable mesh 30 provides a formable mesh 30 that can be shaped along very complex three-dimensional surfaces or contours of the skull 24 in a substantially smooth manner.

Figure 10:
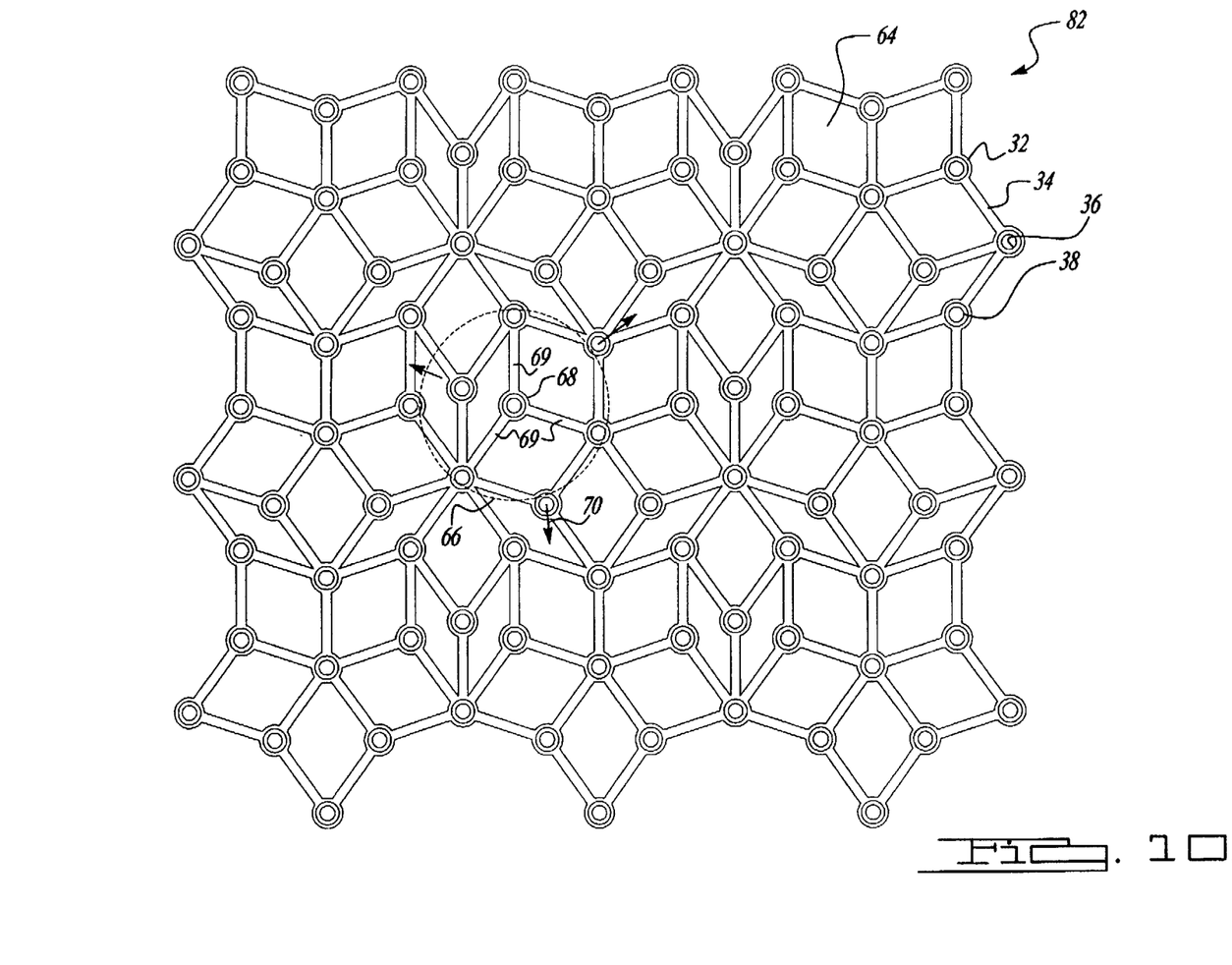
FIG. 10 is a top planar view of the formable mesh according to the teachings of a second preferred embodiment of the present invention.

Referring to FIG. 10, a formable mesh 80 according to the teachings of a second preferred embodiment of the present is shown. In this regard, like reference numerals will used to identify like structures as described with respect to the first preferred embodiment of the present invention. The formable mesh 80 includes the plurality of orifice plates 32 linked together with the plurality of connecting arms 34. The plurality of orifice plates 32 are shown with the circular orifices 36, the counterbores 38, and include the reverse tapers 40. The outer periphery of the orifice plates 32 are shown here formed as a circle. The material and overall dimensions of the formable mesh 80 are similar to the formable mesh 30 of the first preferred embodiment of the present invention.

The formable mesh 80 includes an alternating series of orifice plates 32 having either three (3), four (4), five (5), or seven (7) integrally coupled connecting arms 34. The connecting arms 34 form or define the plurality of quadrilaterals 64, also shown here as parallelograms 64. Upon a close review of FIG. 10, the alternating pattern or series of the three (3) adjacent or contiguous angled parallelograms 66 having a common corner 68 with each sharing a common side 69 are shown. This enables the formable mesh 80 to be shaped or contoured by compressing or expanding the parallelograms 64 along or in at least the three principle directions identified by the arrows 70, similar to the formable mesh 30 in the first preferred embodiment.

The series of orifice plates 32 having the three (3), four (4), five (5), or seven (7) integrally coupled connecting arms 34 also forms a series of four (4), five (5) and seven (7) adjacent or contiguous quadrilaterals or parallelograms 64. Each of these contiguous parallelograms 64 also includes a substantially common corner or center, with each sharing a common adjacent side. In other words, the formable mesh 80 includes an alternating series of three (3), four (4), five (5) and seven (7) contiguous parallelograms 64 which enables movement or displacement along many different planes (i.e. three, four, five and seven) by merely expanding or compressing the parallelograms 64. Moreover, the connecting arms 34 are shown coupled substantially perpendicular to the orifice plates 32 and the quadrilaterals 64 are shown as parallelograms. However, those skilled in the art would recognize that the connecting arms 34 may be angled off counter-clockwise to achieve the self-tightening feature, as shown in FIG. 7, and the quadrilaterals 64 may have various four-sided shapes.

Figure 11:
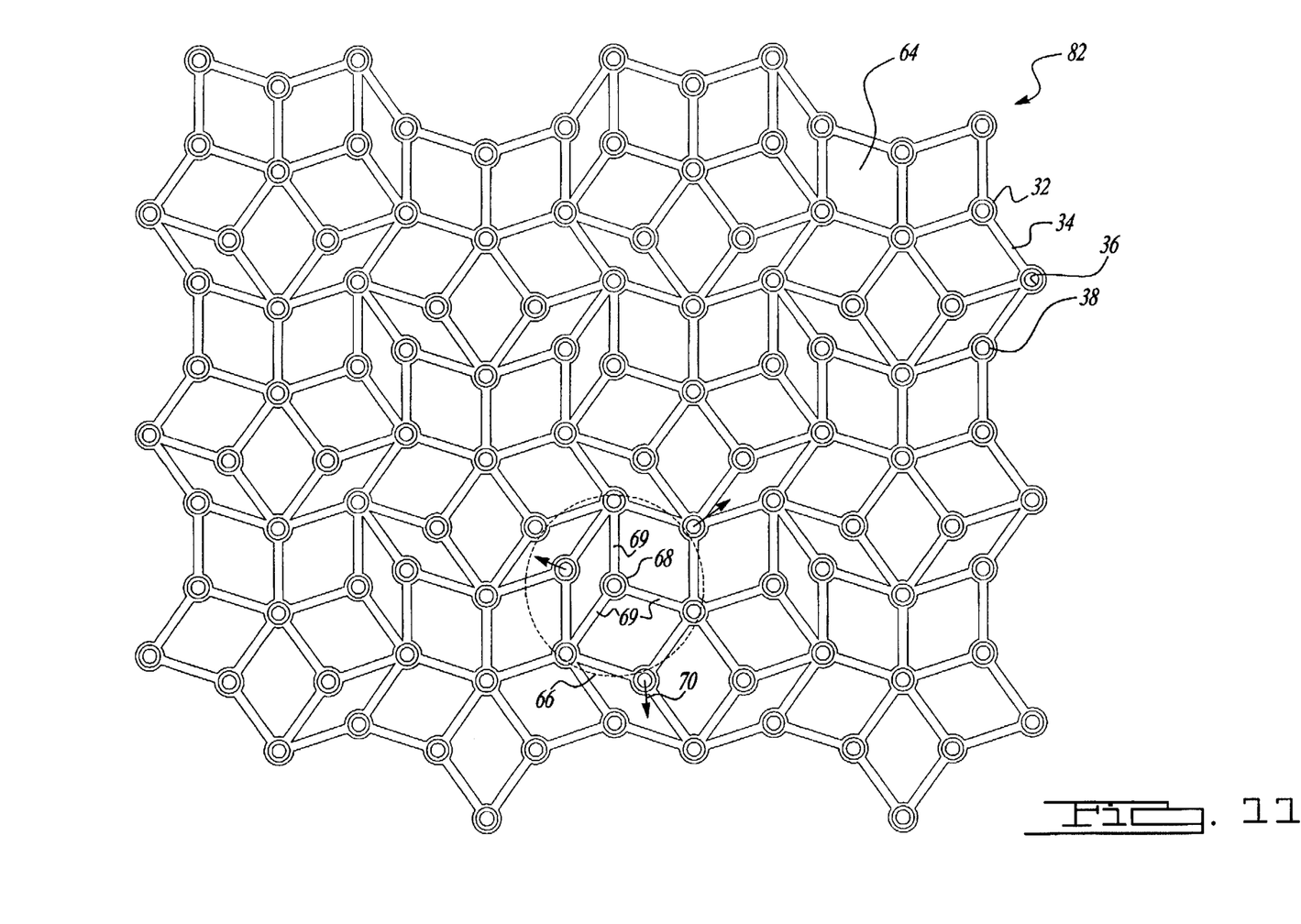
FIG. 11 is a top planar view of the formable mesh according to the teachings of a third preferred embodiment of the present invention.

Referring to FIG. 11, a formable mesh 82 according to the teachings of a third preferred embodiment of the present is shown. In this regard, like reference numerals will be used to identify like structures as described with respect to the first and second preferred embodiments of the present invention. The formable mesh 82 also includes the plurality of orifice plates 32 linked together with the plurality of connecting arms 34. The plurality of orifice plates 32 also include the orifices 36, the counterbores 38, and the reverse tapers 40, with the outer periphery of the orifice plates 32 shown as a circle. Here again, the material and the overall dimensions of the formable mesh 82 are similar to the formable mesh 30 of the first preferred embodiment.

The formable mesh 82 includes an alternating series of orifice plates 32 either having three (3) or five (5) integrally coupled connecting arms 34. The connecting arms 34 also form and define the plurality of quadrilaterals or parallelograms 64. Upon a close review of FIG. 11, the alternating pattern or series of the three (3) adjacent or contiguous angled parallelograms 66 having a common adjacent corner or center 68 with each sharing the common side 69 is shown. In addition, an alternating pattern or series of five (5) contiguous angled quadrilaterals or parallelograms 64 having a common adjacent corner with each sharing a common side is also shown. This alternating series of three (3) and five (5) contiguous parallelograms 64 enables the formable mesh 82 to be shaped or contoured along complex three-dimensional surfaces by expanding or compressing the parallelograms 64 along various directions (i.e. along a series of three and five directions), including at least the three principle directions identified by arrows 70. Here again, those skilled in the art would also recognize that the connecting arms 34 may be angled off counter-clockwise to achieve the self-tightening feature, as shown in FIG. 7.

Figure 12:
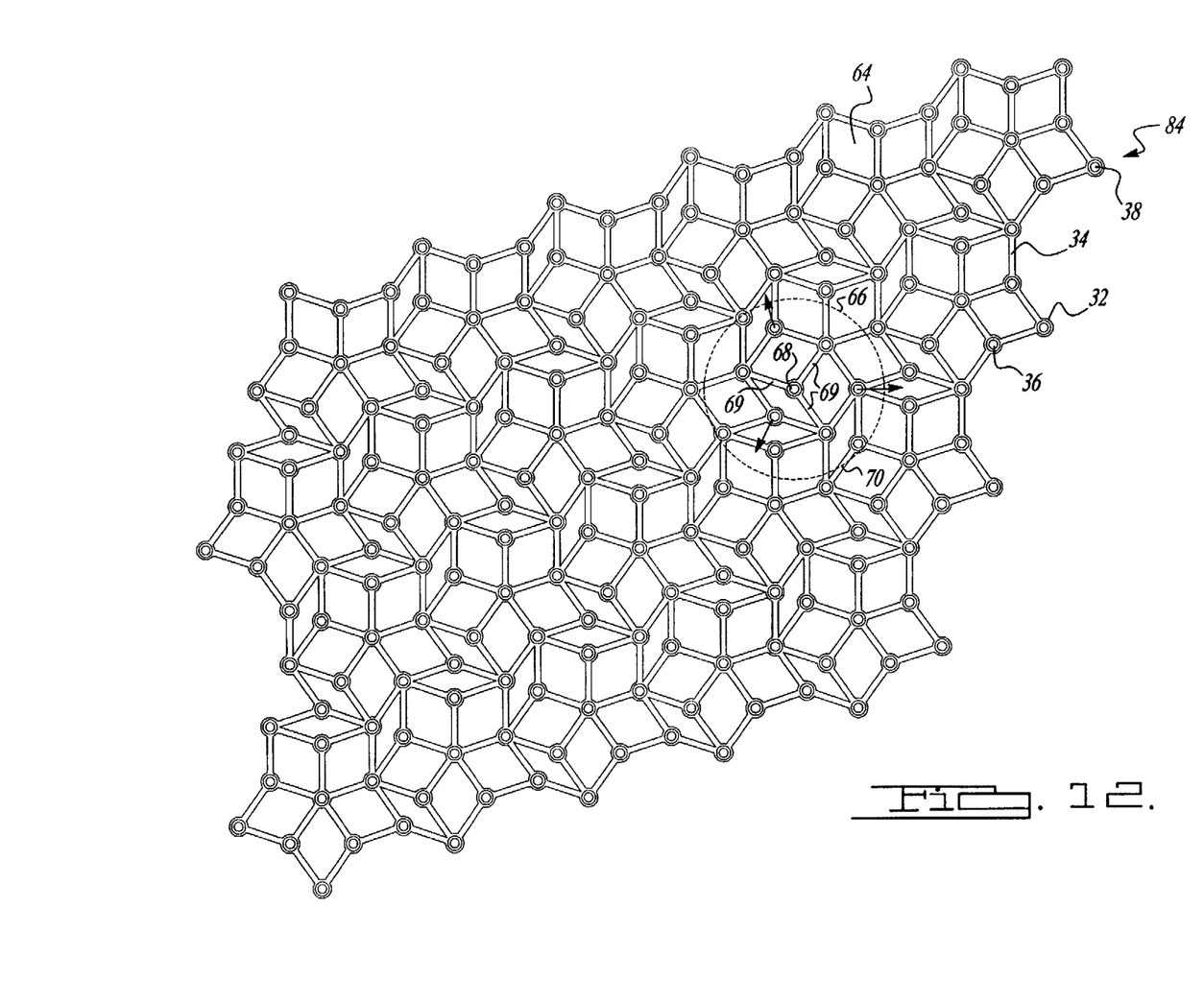
FIG. 12 is a top planar view of the formable mesh according to the teachings of a fourth preferred embodiment of the present invention.

Referring now to FIG. 12, a formable mesh 84 according to the teachings of a fourth preferred embodiment of the present invention is shown. In this regard, like reference numerals will be used to identify like structures as described with respect to the other preferred embodiments of the present invention. The formable mesh 84 includes the plurality of orifice plates 32 linked together with the plurality of connecting arms 34. The plurality of orifice plates 32 include the orifices 36, the counterbores 38 and the reverse tapers 40, with the outer periphery of the orifice plates 32 shown as a circle. Here again, the material and overall dimensions of the formable mesh 84 are similar to the formable mesh 30 of the first preferred embodiment.

The formable mesh 84 also includes an alternating series of orifice plates 32 having either three (3) or five (5) integrally coupled connecting arms 34, similar to FIG. 11. The connecting arms 34 form and define the plurality of quadrilaterals or parallelograms 64. The parallelograms 64 form the alternating pattern or series of the three (3) adjacent or continuous angled parallelograms 66 having a common corner 68 with each sharing a common side 69, as well as a series of five (5) adjacent or continuous angled quadrilaterals or parallelograms 64 having a common corner with each sharing a common adjacent side. This alternating series of three (3) and five (5) parallelograms 64 enables the formable mesh 84 to be shaped or contoured by compressing or expanding the parallelograms 64 along numerous directions including the at least three principle directions identified by the arrows 70. Here again, the connecting arms 34 may also be angled off in FIG. 12 counter-clockwise similar to that shown in FIG. 7 to achieve the self-tightening feature and the quadrilaterals 64 may have numerous four-sided configurations.

The method of using the formable mesh 80, 82 or 84 of the second, third and fourth preferred embodiments is similar to that described with respect to the first preferred embodiment. In this regard, a surgeon first determines the size of the formable mesh required to cover the desired surface area of the bone. Once a size is determined, the surgeon selects the proper size formable mesh or will cut the required size along the connecting arms 34. The surgeon will then form the formable mesh by compressing and expanding the formable mesh along at least the three principle axes of the three contiguous parallelograms 64 by compressing and expanding the parallelograms 64. Should the connecting arms be angled off counter-clockwise, as shown in FIG. 7, upon inserting mounting screws 44 within the orifice plates 32, the automatic self-tightening feature is achieved, similar to that shown in FIG. 7. Otherwise, the mounting screws 44 are merely inserted into the orifice plates 32 after the formable mesh is contoured to the three dimension surface by compressing and expanding the parallelograms 64.

The foregoing discussion discloses and describes merely exemplary embodiments of the present invention. One skilled in the art will readily recognize from such discussion, and from the accompanying drawings and claims, that various changes, modifications and variations can be made therein without departing from the spirit and scope of the invention.

What is claimed is:

1. A formable mesh for use in osteosynthesis, said formable mesh comprising:

a plurality of orifice plates linked together by a plurality of connecting arms;

said plurality of orifice plates includes a first orifice plate having at least six radially offset connecting arms;

each of said at least six radially offset connecting arms having a first end coupled to said first orifice plate and a second end coupled to a second orifice plate;

whereby upon rotation of said first orifice plate in a first direction with a mounting screw, each of said second orifice plates is retracted relative to said first orifice plate and said formable mesh is automatically tightened along a three-dimensional contour.

2. The formable mesh as defined in claim 1 wherein each of said second orifice plates includes three radially offset connecting arms.

3. The formable mesh as defined in claim 2 wherein said first orifice plate having at least six radially offset connecting arms and each of said second orifice plates having three radially offset connecting arms forms a plurality of parallelograms, said plurality of parallelograms operable to be compressed and expanded.

4. The formable mesh as defined in claim 1 wherein said plurality of orifice plates linked together by said plurality of connecting arms forms a plurality of parallelograms, said plurality of parallelograms operable to be compressed and expanded to conform said formable mesh to a three-dimensional contour.

5. A formable mesh as defined in claim 4 wherein said plurality of parallelograms is operable to enable said formable mesh to be compressed or expanded along at least three principle directions.

6. The formable mesh as defined in claim 1 wherein upon rotation of said first orifice plate in a second direction, each of said second orifice plates is extended relative to said first orifice plate.

7. The formable mesh as defined in claim 1 wherein said at least six radially offset connecting arms are pre-rotated and angled off said first orifice plate counter-clockwise.

8. A formable mesh for use in osteosynthesis, said formable mesh comprising:

a plurality of first orifice plates, each of said first orifice plates directly coupled to at least six connecting arms;

a plurality of second orifice plates, each of said second orifice plates directly coupled to only three connecting arms; and each of said connecting arms directly coupling a first orifice plate and a second orifice plate to form a plurality of parallelograms, wherein said plurality of parallelograms are operable to be compressed and expanded to conform said formable mesh to a three-dimensional surface.

9. The formable mesh as defined in claim 8 wherein each of said first orifice plates having said at least six connecting arms are each radially offset from said first orifice plate in a counter-clockwise direction and wherein each of said second orifice plates having said three connecting arms are each radially offset from said second orifice plates in a counter-clockwise direction.

10. The formable mesh as defined in claim 8 wherein upon rotation of a first orifice plate in a first direction, a plurality of second orifice plates are retracted relative to said first orifice plate.

11. The formable mesh as defined in claim 10 whereupon rotation of said first orifice plate in said first direction with a mounting screw automatically tightens said formable mesh along said three-dimensional surface.

12. The formable mesh as defined in claim 8 wherein said plurality of parallelograms includes a plurality of three contiguous parallelograms operable to be compressed and expanded in at least three principle directions.

13. A formable mesh for use in osteosynthesis, said formable mesh comprising:

a first orifice plate having a plurality of first tangentially extending connecting arms;

each of said first tangentially extending connecting arms having a first end coupled to said first orifice plate and a second end coupled to a second orifice plate, each of said second orifice plates coupled to a plurality of second connecting arms; and whereby upon rotation of said first orifice plate in a first direction, each of said second orifice plates is retracted relative to said first orifice plate and upon rotation of said first orifice plate in a second direction, each of said second orifice plates is extended relative to said first orifice plate.

14. The formable mesh as defined in claim 13 wherein each of said second orifice plates includes at least three connecting arms.

15. The formable mesh as defined in claim 13 wherein said first orifice plate coupled to said second orifice plates by said plurality of first tangentially extending connecting arms forms a plurality of parallelograms, said plurality of parallelograms operable to be compressed and expanded to conform said formable mesh to a three-dimensional surface.

16. The formable mesh as defined in claim 13 wherein upon rotation of said first orifice plate in said first direction with a mounting screw, said formable mesh is automatically tightened along a three-dimensional surface.

17. A formable mesh for use in osteosynthesis, said formable mesh comprising:

a plurality of orifice plates;

a plurality of connecting arms linking together said plurality of orifice plates; and said plurality of connecting arms substantially forming a plurality of parallelograms, said plurality of parallelograms forming a plurality of three contiguous parallelograms, each of said three contiguous parallelograms having a common corner with respect to each of said three contiguous parallelograms and each of said three contiguous parallelograms sharing two common adjacent sides with respect to two of said three contiguous parallelograms, wherein said plurality of three contiguous parallelograms are operable to be compressed and expanded along three principle directions to conform said formable mesh to a three-dimensional contour.

18. The formable mesh as defined in claim 17 wherein said plurality of orifice plates includes a plurality of first orifice plates each having six integrally coupled connecting arms and a plurality of second orifice plates each having three integrally coupled connecting arms.

19. The formable mesh as defined in claim 18 wherein each of said first orifice plates having said six connecting arms are each radially offset from said first orifice plates in a counter-clockwise direction and wherein each of said second orifice plates having said three connecting arms are each radially offset from said second orifice plates in a counter-clockwise direction.

20. The formable mesh as defined in claim 18 wherein upon rotation of a first orifice plate in a first direction, a plurality of second orifice plates are retracted relative to said first orifice plate.

21. A formable mesh for use in osteosynthesis, said formable mesh comprising:

a plurality of orifice plates;

a plurality of connecting arms linking together said plurality of orifice plates; and said plurality of connecting arms substantially forming a plurality of quadrilaterals, said plurality of quadrilaterals forming a series of three contiguous quadrilaterals each having a common corner and each sharing a common side, wherein said series of three contiguous quadrilaterals are operable to be compressed and expanded along three principle directions to conform said formable mesh to a three-dimensional contour, whereupon rotation of a first orifice plate in a first direction with a mounting screw automatically tightens said formable mesh along said three-dimensional contour and a plurality of second orifice plates are retracted relative to said first orifice plate.

22. The formable mesh as defined in claim 17 wherein said plurality of parallelograms forms said plurality of three contiguous parallelograms and forms a plurality of four or more contiguous parallelograms each of said four or more contiguous parallelograms having a common corner with respect to each of said four or more contiguous parallelograms and each of said four or more contiguous parallelograms sharing two common adjacent sides with respect to two of said four or more contiguous parallelograms.

23. The formable mesh as defined in claim 17 wherein said plurality of orifice plates includes a plurality of first orifice plates each having five integrally coupled connecting arms and a plurality of second orifice plates each having three integrally coupled connecting arms.

24. A formable mesh for use in osteosynthesis, said formable mesh comprising:

a plurality of orifice plates;

a plurality of connecting arms linking together said plurality of orifice plates; and said plurality of connecting arms substantially defining a plurality of parallelograms, said plurality of parallelograms forming a first plurality of three contiguous parallelograms, each of said three contiguous parallelograms having a common corner with respect to each of said three contiguous parallelograms and each of said three contiguous parallelograms sharing two common adjacent sides with respect to two of said three contiguous parallelograms and a second plurality of at least four contiguous parallelograms, each of said at least four contiguous parallelograms having a common corner with respect to each of said at least four contiguous parallelograms and each of said at least four contiguous parallelograms sharing two common adjacent sides with respect to two of said at least four contiguous parallelograms, wherein said first plurality of three contiguous parallelograms and said second plurality of at least four contiguous parallelograms are operable to be compressed and expanded along multiple directions to conform said formable mesh to a three-dimensional contour.

25. The formable mesh as defined in claim 24 wherein said plurality of orifice plates includes a plurality of first orifice plates each having three integrally coupled connecting arms and a plurality of second orifice plates each having five integrally coupled connecting arms.

26. The formable mesh as defined in claim 24 wherein said plurality of orifice plates includes a plurality of first orifice plates each having six integrally coupled connecting arms and a plurality of second orifice plates each having three integrally coupled connecting arms.

27. A formable mesh for use in osteosynthesis, said formable mesh comprising:

a plurality of orifice plates;

a plurality of connecting arms linking together said plurality of orifice plates, said plurality of orifice plates linked together by said plurality of connecting arms forms a plurality of parallelograms;

each of said orifice plates includes a plurality of integrally coupled connecting arms pre-rotated and angled off from each of said orifice plates in a counter-clockwise direction, whereby upon rotating any one of said orifice plates in a clockwise direction, said formable mesh is automatically compressed in an area adjacent to said rotated orifice plate to conform to a surface contour and whereby said plurality of parallelograms are operable to be compressed and expanded to conform said formable mesh to said surface contour.

28. The formable mesh as defined in claim 27 wherein said plurality of orifice plates includes a plurality of first orifice plates each having six integrally coupled connecting arms and a plurality of second orifice plates each having three integrally coupled connecting arms.

29. The formable mesh as defined in claim 27 wherein upon rotation of a first orifice plate in a first direction, a plurality of second orifice plates are retracted relative to said first orifice plate.

30. A method for aligning and stabilizing bone fragments, said method comprising the steps of:

providing a formable mesh having a plurality of parallelograms forming a plurality of three contiguous parallelograms each having a common corner and each sharing a common side;

compressing and expanding said plurality of parallelograms to generally conform said formable mesh along a three-dimensional contour; and inserting mounting screws in a plurality of orifice plates adjacent to corners of said parallelograms, whereby upon tightening said mounting screws, said formable mesh is of a configuration so that it is automatically compressed and tightened down against said three-dimensional contour.

31. The method as defined in claim 30 further including the step of cutting along a plurality of connecting arms to provide a properly sized formable mesh.

\* \* \* \* \*